United States Patent
Pinchuk

(10) Patent No.: US 9,889,042 B2
(45) Date of Patent: *Feb. 13, 2018

(54) METHOD, SURGICAL KIT AND DEVICE FOR TREATING GLAUCOMA

(71) Applicant: INNFOCUS, INC., Miami, FL (US)

(72) Inventor: Leonard Pinchuk, Miami, FL (US)

(73) Assignee: INNFOCUS, INC., Miami, FL (US)

( * ) Notice: Subject to any disclaimer, the term of this patent is extended or adjusted under 35 U.S.C. 154(b) by 383 days.

This patent is subject to a terminal disclaimer.

(21) Appl. No.: 14/815,084

(22) Filed: Jul. 31, 2015

(65) Prior Publication Data

US 2015/0335486 A1    Nov. 26, 2015

Related U.S. Application Data

(63) Continuation of application No. 13/348,931, filed on Jan. 12, 2012, now Pat. No. 9,101,444.

(51) Int. Cl.
| | | |
|---|---|---|
| A61M 5/00 | (2006.01) | |
| A61F 9/007 | (2006.01) | |
| A61F 9/008 | (2006.01) | |
| A61F 9/00 | (2006.01) | |
| A61M 27/00 | (2006.01) | |

(52) U.S. Cl.
CPC .......... *A61F 9/00781* (2013.01); *A61F 9/007* (2013.01); *A61F 9/00736* (2013.01); *A61F 9/0017* (2013.01); *A61F 2009/00891* (2013.01); *A61M 27/002* (2013.01); *A61M 2210/0612* (2013.01)

(58) Field of Classification Search
CPC .. A61F 9/00781; A61F 9/007; A61F 9/00736; A61F 2009/00; A61F 2009/00891; A61F 9/0017; A61M 27/002; A61M 2210/0612; A61B 17/3415

USPC .......................................................... 604/8
See application file for complete search history.

(56) References Cited

U.S. PATENT DOCUMENTS

| | | |
|---|---|---|
| 3,726,284 A | 4/1973 | Parker |
| 4,011,870 A | 3/1977 | Goldstein |
| 4,276,394 A | 6/1981 | Kennedy et al. |
| 4,316,973 A | 2/1982 | Kennedy |
| 4,342,849 A | 8/1982 | Kennedy |
| 4,762,519 A | 8/1988 | Frimberger |
| 4,787,885 A | 11/1988 | Binder |
| 4,897,255 A | 1/1990 | Fritzberg et al. |
| 4,910,321 A | 3/1990 | Kennedy et al. |
| 4,929,683 A | 5/1990 | Kennedy et al. |
| 4,946,436 A | 8/1990 | Smith |
| 4,946,899 A | 8/1990 | Kennedy et al. |
| 5,066,730 A | 11/1991 | Kennedy et al. |

(Continued)

FOREIGN PATENT DOCUMENTS

| | | |
|---|---|---|
| WO | WO 2005/055873 | 6/2005 |
| WO | WO2007/087061 A2 | 8/2007 |

*Primary Examiner* — Tatyana Zalukaeva
*Assistant Examiner* — Kai Weng
(74) *Attorney, Agent, or Firm* — Gordon & Jacobson, P.C.

(57) ABSTRACT

A surgical kit includes at least one instrument and at least one implant device. The instrument has a needle body used to form a surgical passage through ocular tissue. The device includes a flexible tube that defines a duct for diverting aqueous humor with an outer surface having a maximal cross-sectional dimension that is less than the maximal cross-sectional dimension of the needle body. The device incorporates a seal that defines a maximal cross-sectional dimension that is greater that the maximal cross-sectional dimension of the needle body and is operably disposed within the surgical passage and forms a seal between the surrounding ocular tissue. The kit (and devices thereof) can be used as part of a surgical method to divert aqueous humor to a space formed in ocular tissue.

19 Claims, 11 Drawing Sheets

(56) References Cited

U.S. PATENT DOCUMENTS

| | | | |
|---|---|---|---|
| 5,122,572 | A | 6/1992 | Kennedy et al. |
| RE34,640 | E | 6/1994 | Kennedy et al. |
| 5,733,925 | A | 3/1998 | Kunz et al. |
| 5,741,331 | A | 4/1998 | Pinchuk |
| 6,007,510 | A | 12/1999 | Nigam |
| 6,007,511 | A | 12/1999 | Prywes |
| 6,010,461 | A | 1/2000 | Haniff et al. |
| 6,050,970 | A | 4/2000 | Baerveldt |
| 6,102,939 | A | 8/2000 | Pinchuk |
| 6,197,240 | B1 | 3/2001 | Pinchuk |
| 6,468,283 | B1 | 10/2002 | Richter et al. |
| 6,545,097 | B2 | 4/2003 | Pinchuk et al. |
| 6,666,841 | B2 | 12/2003 | Gharib et al. |
| 6,881,198 | B2 | 4/2005 | Brown |
| 6,966,888 | B2 | 11/2005 | Cullen et al. |
| 7,431,709 | B2 | 10/2008 | Pinchuk et al. |
| 7,559,952 | B2 | 7/2009 | Pinchuk |
| 7,594,899 | B2 | 9/2009 | Pinchuk et al. |
| 7,662,123 | B2 | 2/2010 | Shields |
| 7,670,310 | B2 | 3/2010 | Yaron et al. |
| 7,708,711 | B2 | 5/2010 | Tu et al. |
| 7,837,644 | B2 | 11/2010 | Pinchuk et al. |
| 2004/0147870 | A1 | 7/2004 | Burns et al. |
| 2007/0027470 | A1 | 2/2007 | Dodick |
| 2007/0118065 | A1 | 5/2007 | Pinchuk et al. |
| 2009/0043328 | A1 | 2/2009 | Delsman |
| 2009/0124773 | A1 | 5/2009 | Zhou et al. |
| 2009/0177219 | A1 | 7/2009 | Conlon |
| 2013/0184631 | A1 | 7/2013 | Pinchuk |

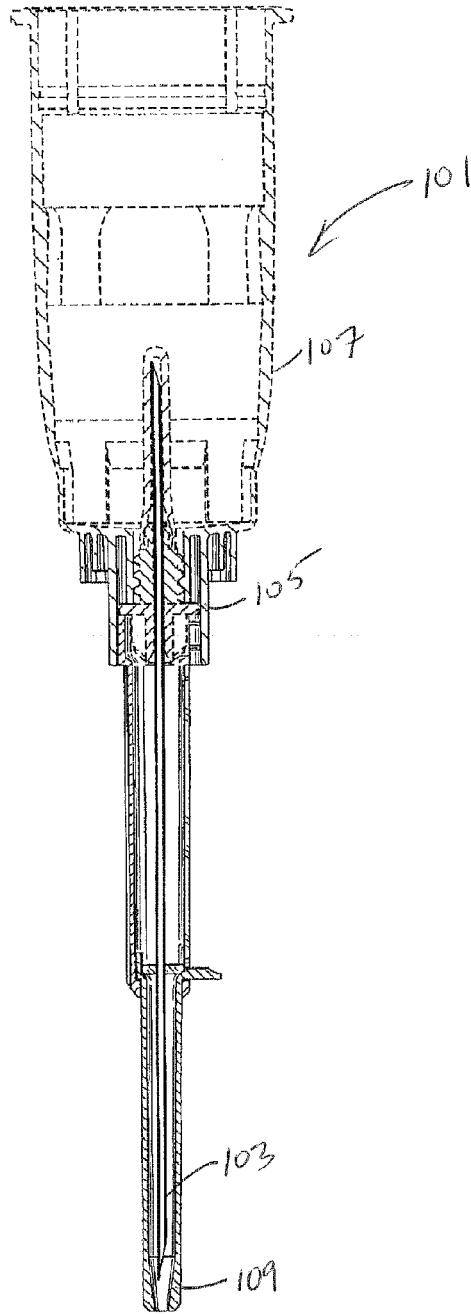
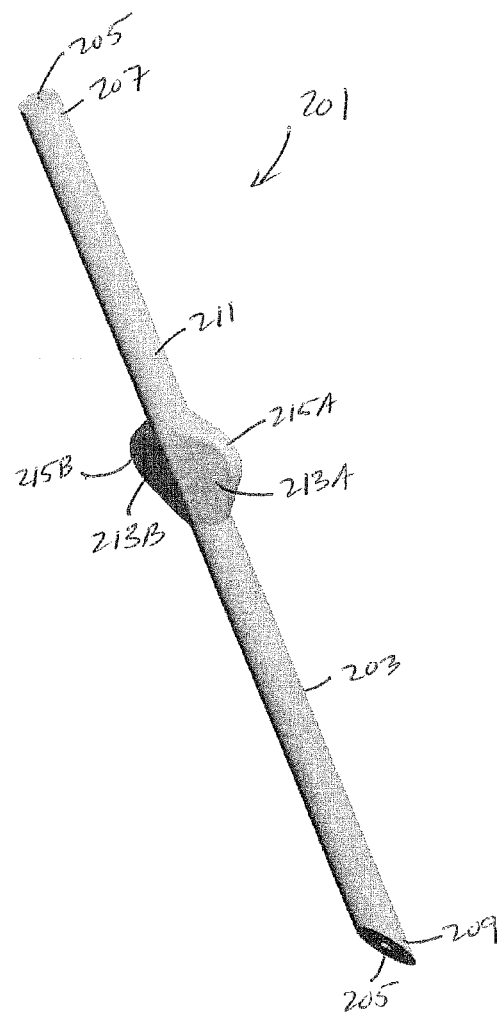
FIG. 2
FIG. 3

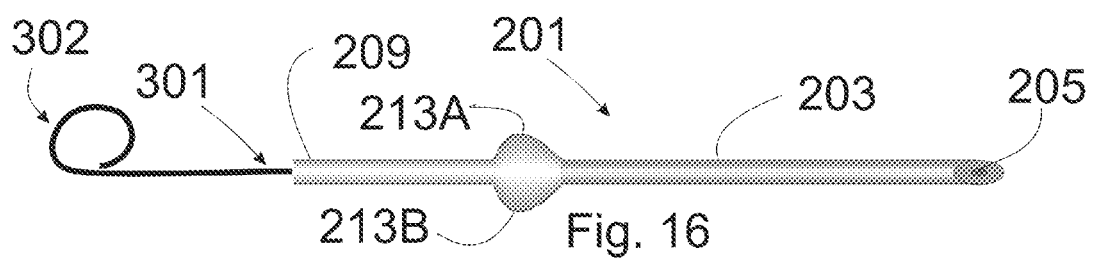
Fig. 16
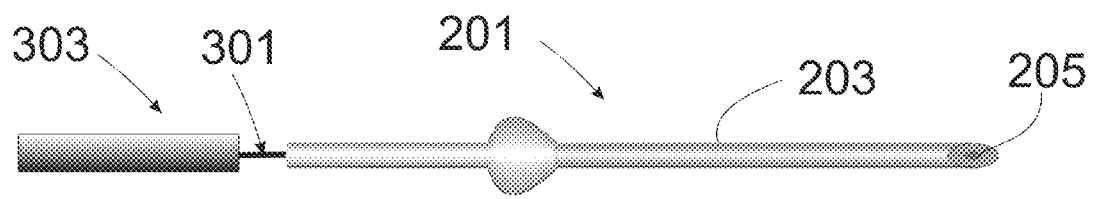
Fig. 17
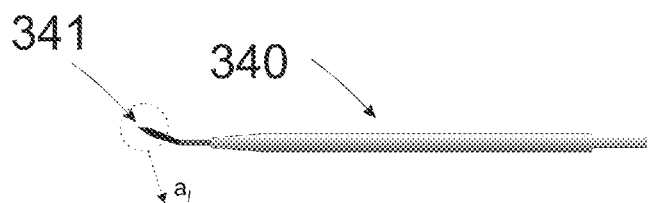
Fig. 18A
Fig. 18B
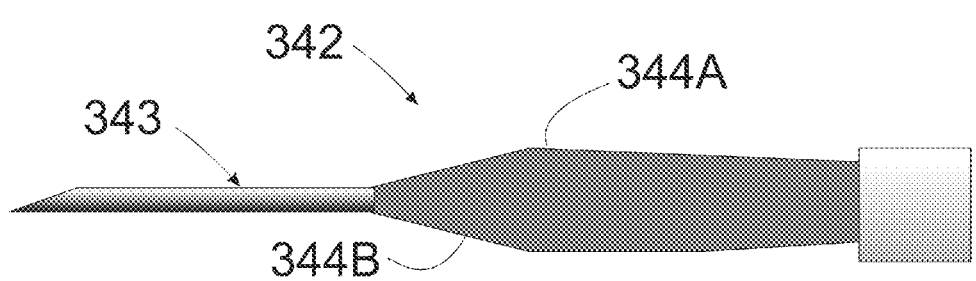
Fig. 18C

METHOD, SURGICAL KIT AND DEVICE FOR TREATING GLAUCOMA

CROSS-REFERENCE TO RELATED APPLICATION

This application is a continuation of U.S. Ser. No. 13/348,931, filed Jan. 12, 2012, which is hereby incorporated by reference herein in its entirety.

BACKGROUND OF THE INVENTION

1. Field of the Invention

The present invention relates to surgical treatment of glaucoma. More particularly, this invention relates to medical devices and materials for diverting aqueous humor out of the anterior chamber through a surgically implanted duct passageway.

2. State of the Art

Glaucoma is a progressive ocular disease that manifests itself through elevated intraocular pressure ("IOP"). High pressure develops in an eye because of impaired outflow of aqueous humor. In open-angle glaucoma, the impaired outflow is caused by abnormalities of the drainage system of the anterior chamber. In closed-angle glaucoma, the impaired outflow is caused by impaired access of aqueous to the drainage system. If the pressure within the eye remains sufficiently high for a long enough period of time, total vision loss occurs. Thus, glaucoma is a leading cause of preventable blindness.

As shown in FIG. 1, the eye 10 is a hollow structure wherein the anterior chamber 20 contains a clear fluid called aqueous humor. Aqueous humor is formed by the ciliary body 12 adjacent the posterior chamber 9 of the eye. The fluid, which is made at a fairly constant rate, then passes around the lens 14, through the pupillary opening in the iris 18 and into the anterior chamber 20. Once in the anterior chamber 20, the fluid drains out of the eye 10 through two different routes. In the uveoscleral route, the fluid percolates between muscle fibers of the ciliary body 12. This route accounts for approximately ten percent of the aqueous outflow in humans. The primary pathway for aqueous outflow in humans is through the canalicular route, which involves the trabecular meshwork (not shown) and Schlemm's canal 24.

The trabecular meshwork and Schlemm's canal 24 are located at the junction between the iris 18 and the sclera 26. This junction, which is typically referred to as the angle, is labeled 28. The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal 24 is disposed adjacent to the trabecular meshwork. The outer wall of the trabecular meshwork coincides with the inner wall of Schlemm's canal 24. Schlemm's canal 24 is a tube-like structure that runs around the circumference of the cornea. In human adults, Schlemm's canal is believed to be divided by septa into a series of autonomous, dead-end canals. The aqueous fluid travels through the spaces between the trabecular beams of the trabecular meshwork, across the inner wall of Schlemm's canal 24 into the canal, through a series of collecting channels that drain from Schlemm's canal 24 and into the episcleral venous system (not shown).

The tough outer membrane known as the sclera 26 covers all of the eye 10 except that portion covered by the cornea 34, which is the thin, transparent membrane which covers the pupillary opening and the iris 18. The cornea 34 merges into the sclera 26 at a juncture referred to as the limbus 32. A portion of the sclera 26 is covered by a thin tissue called Tenon's membrane 36 (also called Tenon's capsule), which envelopes the bulb of the eye from the optic nerve (not shown) to the ciliary region. Near its front, Tenon's membrane 36 blends into the conjunctiva 30 where it is attached to the ciliary region of the eye as shown.

In a normal patient, aqueous humor production is equal to aqueous humor outflow and intraocular pressure remains fairly constant (typically in the 8 to 18 mmHg range). In glaucoma, there is abnormal resistance to aqueous humor outflow, which manifests itself as increased IOP. Tonometry is the measurement of IOP. In primary open angle glaucoma, which is the most common form of glaucoma, the abnormal resistance is believed to be along the outer aspect of trabecular meshwork and the inner wall of Schlemm's canal 24. Primary open angle glaucoma accounts for approximately eighty-five percent of all glaucoma. Other forms of glaucoma (such as angle closure glaucoma and secondary glaucomas) also involve decreased aqueous humor outflow through the canalicular pathway but the increased resistance is from other causes such as mechanical blockage, inflammatory debris, cellular blockage, etc.

With the increased resistance, the aqueous humor builds up because it cannot exit fast enough. As the aqueous humor builds up, the IOP within the eye increases. The increased IOP compresses the axons in the optic nerve and also may compromise the vascular supply to the optic nerve. The optic nerve carries vision from the eye to the brain. Some eyes seem more susceptible to damage from excessive IOP than other eyes. While research is investigating ways to protect the nerve from an elevated pressure, the therapeutic approach currently available in glaucoma is to reduce the intraocular pressure.

The clinical treatment of glaucoma is typically carried out in a step-wise manner. Medication often is the first treatment option. Administered either topically or orally, these medications work to either reduce aqueous production or they act to increase outflow. If one medication fails, the patient is oftentimes given a second medication and then a third and fourth. It is not unusual to have glaucoma patients on four separate medications. Currently available medications have many serious side effects including: congestive heart failure, respiratory distress, hypertension, depression, renal stones, aplastic anemia, sexual dysfunction and death. In addition, the preservatives in various medications are known to cause damage to the endothelial cells underlying the cornea which can manifest as opacification of the cornea. Further, the preservatives can also change the characteristics of the conjunctiva which can lead to additional filtration problems. Compliance with medication is a also a major problem, with estimates that over half of glaucoma patients do not follow their correct dosing schedules which can lead to progressive vision loss.

When medication fails to adequately reduce the IOP, laser trabeculoplasty is often performed. In laser trabeculoplasty, thermal energy from a laser is applied to a number of noncontiguous spots in the trabecular meshwork. It is believed that the laser energy stimulates the metabolism of the trabecular cells in some way, and changes the cellular material in the trabecular meshwork. In a large percent of patients, aqueous humor outflow is enhanced and IOP decreases. However, the effect often does not last long and a significant percentage of patients develop an elevated IOP within the years that follow the treatment. The laser trabeculoplasty treatment is typically not repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the IOP sufficiently, then incisional surgery (typically referred to as filtering surgery) is performed. The most commonly performed incisional procedure is trabeculectomy. The trabeculectomy procedure involves cutting a "trapdoor" in the sclera and then from within the wall of the trapdoor, punching a hole into the anterior chamber which allows fluid to drain from the anterior chamber into the trapdoor, out the "door" of the trapdoor and then into a bleb (a blister-like formation) under the conjunctiva, thereby decreasing IOP. Sutures are placed under controlled tension to keep the door of the trapdoor sufficiently closed in order to control IOP and avoid hypotony (i.e., low IOP). This procedure is relatively difficult to perform correctly and has a high level of long-term complications. Additional interventions often need to be performed to adjust the tension in the sutures to further control IOP.

When trabeculectomy doesn't successfully lower the eye pressure, the next step, and usually the last, is a surgical procedure that implants a glaucoma drainage implant (GDI) that shunts aqueous humor from the anterior chamber to control the IOP. One such GDI, as shown in U.S. Pat. No. 6,050,970 to Baerveldt, is a drainage tube that is attached at one end to a plastic plate. The drainage tube is comprised of a silicone rubber shunt with an outer diameter of between 1.0 and 3.0 French; preferably with an inner diameter of 0.3 mm and an outer diameter of 0.6 mm (1.8 French). The Baerveldt tube is implanted by first making an incision in the conjunctiva 30, exposing the sclera 26 and the natural plane between the sclera and conjunctiva/Tenon's membrane is dissected down to slightly beyond the equator. The plastic plate is sewn to the surface of the sclera posteriorly, usually over the equator. A full thickness hole is made into the eye under the limbus 32, usually with a needle. The tube is inserted into the eye through this needle tract. The external portion of the tube is covered with either cadaver sclera or other equivalent tissue to prevent it from eroding through the conjunctiva. The conjunctiva 30 is replaced and the incision is closed tightly. With this shunt device, aqueous drains out of the anterior chamber through the tube and along the surface of the plate and into the bleb, where the bleb is defined as a thin layer of connective tissue that encapsulates the plate and tube. The plate typically has a large surface area, which can be as large as 20 mm in diameter, in order to wick and disperse fluid. Once fluid accumulates in the bleb, it can absorb through the tissues of the bleb and into the venous system of the sclera or to the surface of the eye where it can evaporate or collect in the tear ducts. These plates are generally made of silicone rubber, which eventually becomes encapsulated by the connective tissue of the bleb. These large encapsulated plates are irritating to some patients.

Some of the current approved GDIs include valving of the tube that enters the anterior chamber of the eye in order to control IOP and avoid hypotony. In addition, many GDI's including the aforementioned Baerveldt valve have their tubes tied off to prevent hypotony in the acute phase before capsules form around the device. The ligating sutures are then cleaved with a laser or dissolve within a month.

Current GDIs have an effective half life of two to five years from implantation before a second, third or fourth GDI is required. Due to the bulky size of current GDIs, there is room for only three devices in the eye; rarely is a fourth device implanted. The problems associated with current generation GDIs are:

Impairment of eye motion and resulting double vision (diplopia).

Hypotony (low IOP which could result in a detached retina).

Erosion of conjunctiva and infection and associated high costs of using a cadaver sclera to prevent erosion. Furthermore, cadaver sclera is difficult to obtain outside the U.S. and several religions do not permit the use of cadaver tissue in the body.

Severe encapsulation of the plate which prevents proper filtering of fluid and leads to poor IOP control.

The difficulty of performing trabeculectomies and GDI's as well as their associated morbidities led to development of a novel glaucoma drainage implant described in U.S. Pat. Nos. 7,431,709; 7,594,899; and 7,837,644; commonly assigned to assignee of the present invention and herein incorporated by reference in their entireties.

SUMMARY OF THE INVENTION

In one embodiment, a kit is provided for treating glaucoma which includes at least one hand-held instrument and at least one aqueous humor drainage device. The hand-held instrument has a needle body that is inserted through ocular tissue into the anterior chamber of the eye to define a passage through the ocular tissue leading to the anterior chamber. It is also contemplated that the entrance through the ocular tissue can be selectively widened by means of a stab wound or by manipulation of the tip of the needle body to better accommodate the aqueous humor drainage device. The needle body has a maximal cross-sectional dimension (e.g., diameter D1 of FIG. 5) along its length.

The aqueous humor drainage device includes a flexible tube that defines a duct for diverting aqueous humor from the anterior chamber. The tube has a proximal end and distal end opposite one another. The distal end can have a tapered profile that facilitates insertion into the passage leading to the anterior chamber formed by the needle body. The tube's outer surface has a maximal cross-sectional dimension (e.g., the outer diameter D2 of FIG. 7) that is less than the maximal cross-sectional dimension of the needle body (e.g., diameter D1 of FIG. 5). The device also incorporates sealing means that includes at least one element that is spaced apart from the proximal and distal ends of the tube and that extends radially outward beyond the outer surface of the tube. The element(s) define a maximal cross-sectional dimension that is greater that the maximal cross-sectional dimension of the needle body (e.g., outer diameter D1 of FIG. 5). The element(s) are operably disposed within the passage defined by the needle body, and their relative dimensions cause the surrounding ocular tissue to directly contact the element(s) in order to form a seal between the surrounding tissue and the element(s). The seal surrounds the entire circumferential perimeter of the device defined by the element(s) and seal prevents leakage of aqueous humor through the space between the tube and the surrounding ocular tissue. The element(s) of the sealing means also act to fix the device in place in the passage and minimize migration of the device in both the proximal and distal directions. The maximum cross-sectional diameter of the element(s) of the sealing means is defined by at least one blunt surface to facilitate sealing.

In one embodiment, the element(s) of the sealing means is realized by two tabs that are disposed opposite one another on opposite sides of the tube. The two tabs can be generally planar in form and lie in a common plane that extends transverse to the central axis of the tube. The generally co-planar configuration of the tabs minimizes the profile of the device in order to reduce erosion and migration of the device. The two tabs can be mirror images of one another reflected about the central axis of the tube. The outer edges of the tabs can have a tapered profile facing the distal end of the tube. This tapered profile facilitates introduction of the tabs into the passage formed by the needle body. The tabs can have a profile that tapers in the radial direction (i.e., the direction of the common plane of the two tabs) transverse to the central axis of the tube.

In one embodiment, the instruments of the kit (including at least one hand-held instrument and at least one aqueous humor drainage device) are housed in one or more enclosures that provide the surgeon easy access to the instruments as needed. The enclosure(s) can be realized from suitable material (such as a thermoplastic) that is inexpensive and readily disposable for one-time use. Other materials (such as stainless steel and the like) suitable for non-disposable applications can also be used.

An inserter can be used to deploy the device into the passage leading to the anterior chamber formed by the needle body. The inserter can be realized by an apparatus similar to that described in U.S. Pat. Nos. 7,431,7091; 7,594,899; and 7,837,644 with one or two slots that accommodate the tabs of the device. Alternatively, the inserter can be realized by a stylet and/or a trocar device as described below. In such embodiments, the inserter can be part of the instrument kit housed in the enclosure.

In another embodiment, one or more elements of the kit can be used as part of a surgical method to divert aqueous humor to a pocket region formed in the ocular tissue (such as a pocket formed between the conjuctiva-sclera and Tenon's membrane).

BRIEF DESCRIPTION OF THE DRAWINGS

FIG. 2 is a schematic view of an embodiment of a hand-held instrument for defining a surgical passage through tissue leading into the anterior chamber of the eye.

FIG. 3 is a perspective view of an embodiment of an aqueous humor drainage device that drains aqueous humor from the anterior chamber of the eye.

FIG. 16 is a schematic view illustrating an embodiment of a stylet and an aqueous humor drainage device, the stylet for use in positioning the aqueous humor drainage device.

FIG. 17 is a schematic view illustrating another embodiment of a stylet and an aqueous humor drainage device, the stylet for use in positioning the aqueous humor drainage device.

FIG. 18A is a schematic illustration of an embodiment of a knife used in a surgical method for treating elevated intraocular pressure, the knife for defining a passage through tissue and in communication with the anterior chamber of the eye.

FIG. 18B is a magnified view of the distal end of the knife of FIG. 18A.

FIG. 18C is a schematic illustration of an embodiment of a hand-held instrument used in a surgical method for treating elevated intraocular pressure, the instrument for defining a passage through tissue and in communication with the anterior chamber of the eye.

DETAILED DESCRIPTION OF THE PREFERRED EMBODIMENTS

Figure 1:
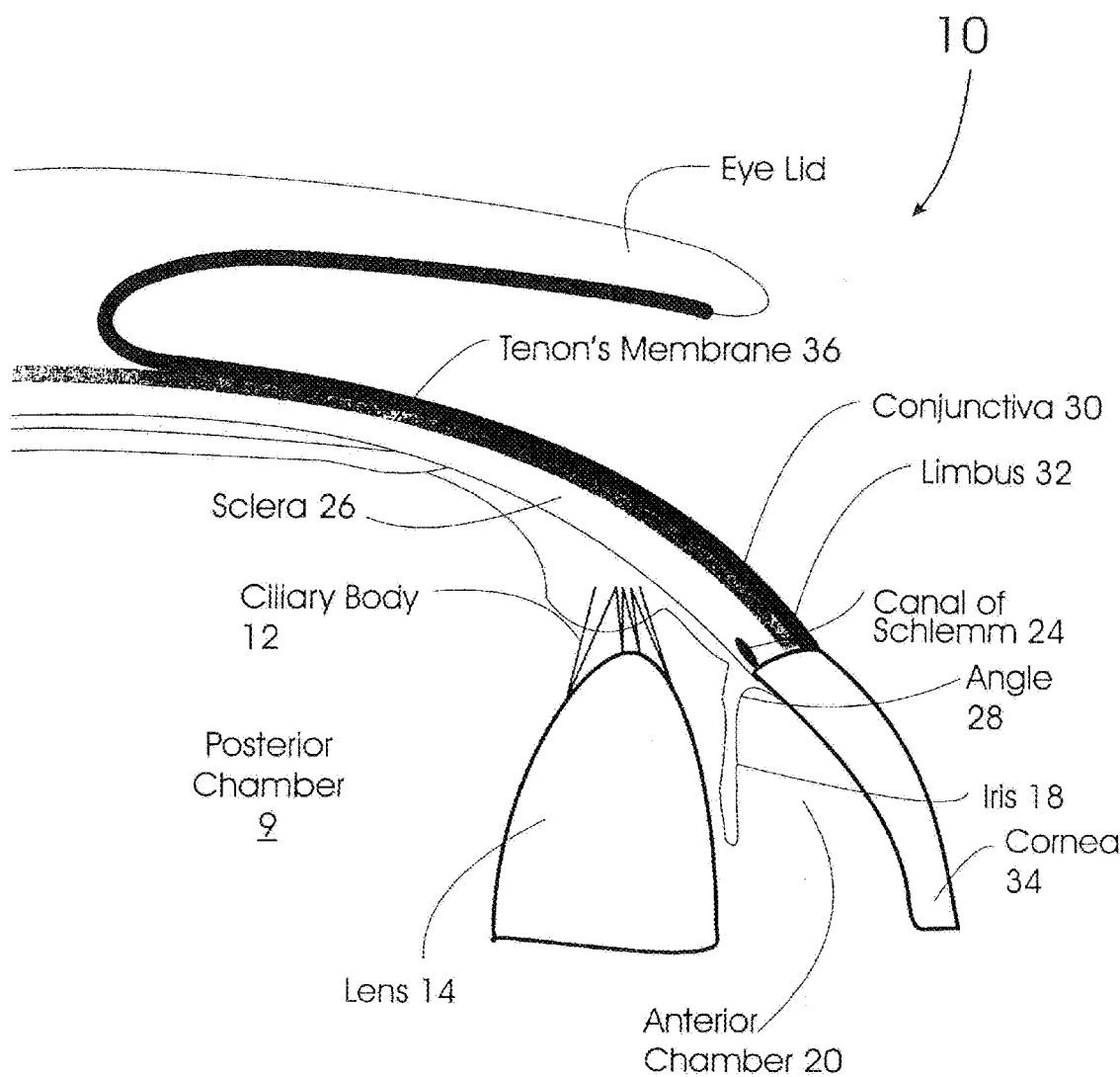
FIG. 1 is an illustration showing anatomic details of the human eye.

As used herein, the term "distal" is generally defined as in the direction of the eye of the patient, or away from a user of the system/apparatus/device. Conversely, "proximal" generally means in the direction away from the eye of the patient, or toward the user of the system/apparatus/device.

Turning now to FIGS. 2 and 3, there is shown an embodiment of a kit for treating glaucoma, which includes at least one hand-held instrument 101 (FIG. 2) and at least one aqueous humor drainage device 201 (FIG. 3). The instrument 101 has a needle body 103 that is inserted through ocular tissue into the anterior chamber 20 of the eye (FIG. 1) to define a passage through the tissue leading into the anterior chamber 20. The needle body 103 has a maximal cross-sectional dimension (e.g., diameter D1 of FIG. 5) along its length. The proximal end of the needle body 103 is rigidly coupled to a hub 105. A handle 107 is rigidly coupled to the hub 105. The handle 107 is gripped by the fingers of the surgeon for manipulation of the needle body 103 as desired. A needle cover 109 can extend over the needle body 103 for safety. The needle body 103 can have a hollow-bore (or possibly a solid bore). The hub 105 and the handle 107 can be realized by a syringe body that includes a plunger that fits inside a tube as is well known. A solution can be loaded into the tube and pumped through the hollow-bore needle body 103 by hand manipulation of the plunger. In addition, the needle body may be bent into a more desirable shape to precisely place the needle tract, especially when the patient's nose is in the way of the needle handle.

The aqueous humor drainage device 201 includes a flexible tube 203 that defines a duct 205 for diverting aqueous humor from the anterior chamber 20. The tube 203 has a proximal end 207 and distal end 209 opposite one another. The distal end 209 can have a tapered profile that facilitates insertion into the passage leading to the anterior chamber 20 formed by the needle body 103. The tube's outer surface 211 has a maximal cross-sectional dimension (e.g., outer diameter D2 of FIG. 7) that is less than the maximal cross-sectional dimension of the needle body 103 (e.g., diameter D1 of FIG. 5). The device 201 also includes first and second tabs or fins 213A, 213B that are spaced apart from the proximal and distal ends 207, 209 of the tube 203. The tabs 213A, 213B extend radially outward beyond the outer surface 211 of the tube 203 opposite one another on opposing sides of the tube 203. The first and second tabs 213A, 213B can be generally planar in form and lie in a common plane that extends transverse to the central axis of the tube 203 as best shown in FIG. 3. The generally co-planar configuration of the tabs 213A, 213B, when placed flat against the sclera of the eye, minimizes the profile of the device in order to reduce erosion and migration. The first and second tabs 213A, 213B can be mirror images of one another reflected about the central axis of the tube 203 as shown. Tab 213A defines an outer edge 215A, and tab 213B defines an outer edge 215B. The maximal distance between the outer edge 215A and the outer edge 215B define a maximal cross-sectional dimension that is greater that the maximal cross-sectional dimension of the needle body 103 (e.g., outer diameter D1 of FIG. 5). The tabs 213A, 213B are operably disposed within the passage defined by the needle body 103 and their dimensions cause the surrounding tissue to directly contact the tabs 213A, 213B in order to form a seal between the surrounding tissue and the tabs 213A, 213B. The seal surrounds the entire circumferential perimeter of the device defined by the tabs 213A, 213B and prevents leakage of aqueous humor through the space between the tube 203 and the surrounding tissue. The needle-defined passage can also be widened in the scleral area with the use of a sharp knife and associated stab wound. The widened part can be formed either before or after formation of the needle-defined passage. The tabs 213A, 213B can deform in the passage as they are inserted into the passage in response to forces applied by the surrounding tissue, and/or the surrounding tissue can deform (by compressing/stretching/thinning) as the tabs 213A, 213B are inserted into the passage. Such deformation is controlled by the maximal cross-sectional dimension of the tabs 213A, 213B relative to the cross-sectional dimension of the passage (as formed by the needle body 103 or stab wound) as well as the hardness of the material of the tabs 213A, 213B. The tabs 213A, 213B also act to fix the device 201 in place in the passage and minimize migration of the device 201 in both the proximal and distal directions.

The outer edges 215A, 215B of the tabs 213A, 213B can have a tapered profile facing the distal end 209 as best shown on FIG. 3. This tapered profile facilitates introduction of the tabs 213A, 213B into the passage formed by the needle body 103.

The tabs 213A, 213B can have respective profiles that taper in the radial direction (i.e., the direction of the common plane of the tabs) transverse to and away from the central axis of the tube 203 as best shown in FIG. 3.

The outer surface 211 of the tube 203 has a maximal cross-sectional dimension (e.g., outer diameter D2) that is less than the maximal cross-sectional dimension of the needle body 103. For example, the outer surface 211 can have an outer diameter D2 less than 0.4 mm (such as on the order of 0.35 mm) for a needle body 103 with a maximal cross-sectional dimension of 0.4 mm. In one embodiment, the duct 205 of the tube 203 is a simple constant-diameter lumen with a diameter in the range between 0.05 mm and 0.15 mm. This small duct diameter limits aqueous humor flow through the tube 203 and provides for control over IOP without the need for unidirectional valves or other structures (such as filters) that limit aqueous humor flow through the tube. More specifically, the diameter of the duct 205 alone controls the flow rate of aqueous humor through the duct 205 and thus controls the IOP of the patient. The appropriate duct diameter can vary among patients depending on the production rate of aqueous humor and the extent of clogging of the natural drainage paths of the patient and thus can be selected by the physician as desired.

Figure 4:
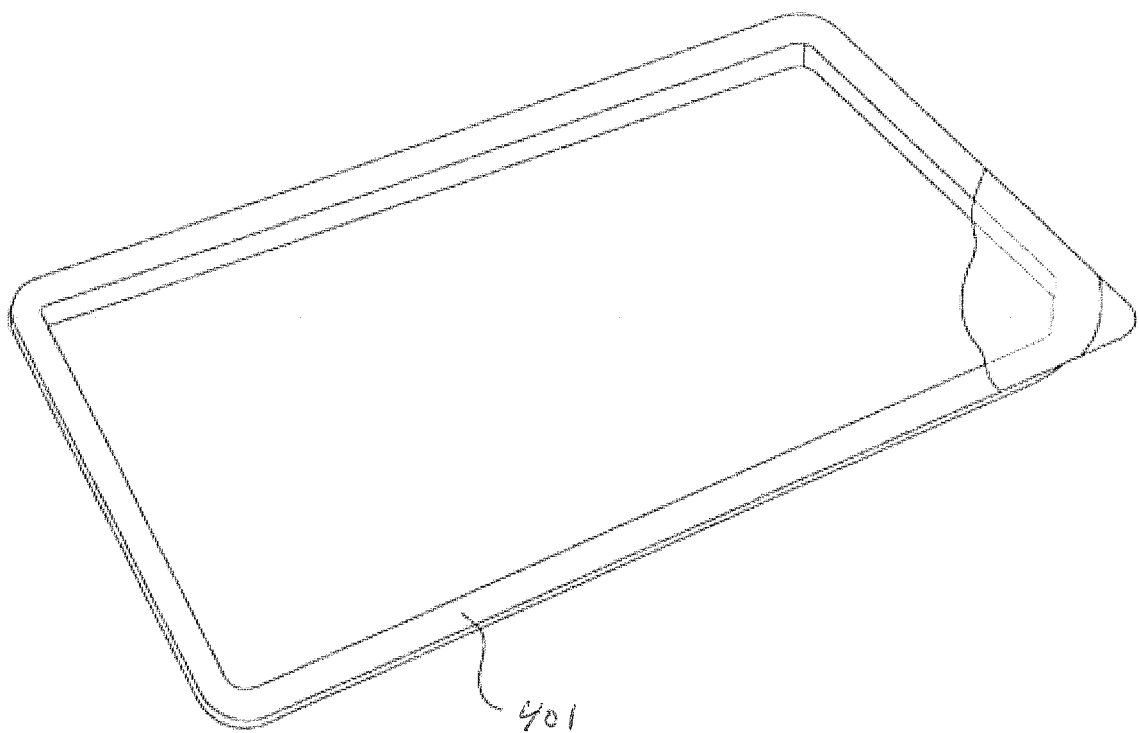
FIG. 4 is a perspective view of an embodiment of a surgical kit enclosure.

In one embodiment, the instruments of a kit, including at least one hand-held instrument 101 (FIG. 2) and at least one aqueous humor drainage device 201 (FIG. 3) as described herein, are housed in one or more enclosures, such as an instrument tray 401 as shown in FIG. 4, that provides the surgeon easy access to the instruments as needed. The instrument tray 401 can be realized from suitable material (such as a thermoplastic) that is inexpensive and readily disposable for one-time use. Other materials (such as stainless steel and the like) suitable for non-disposable applications can also be used. The kit can include a plurality of hand-held instruments 101 (FIG. 2) with needle bodies of different diameters and/or a plurality of aqueous humor drainage devices 201 (FIG. 3) with tube ducts and/or tabs of different sizes (for example, a plurality of devices 201 with different tab sizes that correspond to varying needle body diameters of the instruments 101 of the kit). In addition, to effected the stab incision, knives of different diameters (discussed hereinafter with respect to FIGS. 18A and 18B) can be included in the kit as well as measuring devices, medications, sponges to apply medication, measuring devices, markers, syringes, rinsing fluid, trocars, inserters and the like.

An inserter can be used to deploy the device 201 into the passage leading to the anterior chamber 20 formed by the needle body 103. The inserter can be realized by an apparatus similar to that described in U.S. Pat. Nos. 7,431,709, 7,594,899, and 7,837,644 with one or two slots that accommodate the tabs 213A, 213B of the device 201. Alternatively, the inserter can be realized by a stylet and/or a trocar device as described below. In such embodiments, the inserter can be part of the instrument kit housed in the tray 401.

Figure 5:
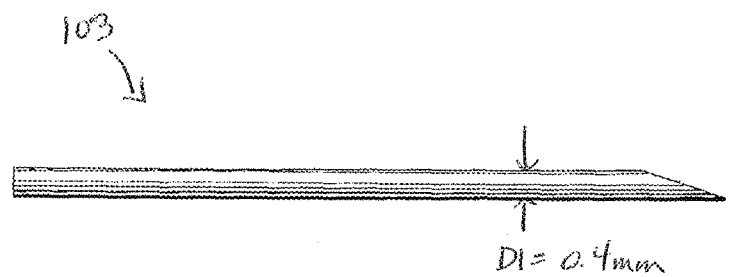
FIG. 5 is a side view of an illustrative embodiment of a needle body that is part of the hand-held instrument of FIG. 2.

FIG. 5 shows the dimensions of an exemplary embodiment of the needle body 103. In this exemplary embodiment, the needle body 103 has an outer diameter D1 of 0.4 mm (i.e., 27 gauge). Other suitable outer diameters D1 can be in the range from 0.4 mm (i.e., 27 gauge) to 0.635 mm (i.e., 23 gauge). The needle body 103 can also be provided bent into a desirable shape to allow the needle to be inserted into the eye at an angle that, if not bent, would interfere with the patient's nose.

Figure 6:
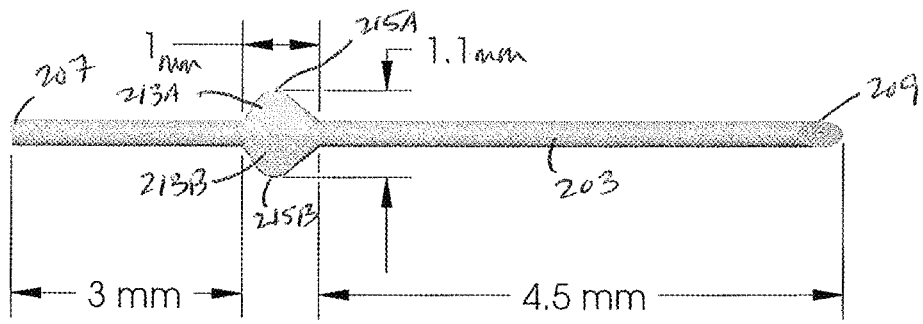
FIG. 6 is a top view of an illustrative embodiment of the aqueous humor drainage device of FIG. 3.
Figure 7:
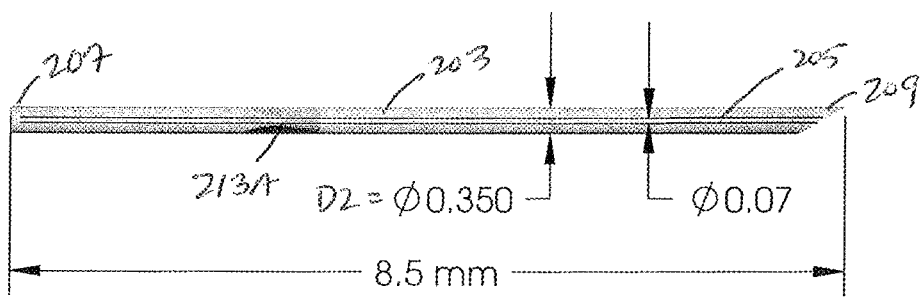
FIG. 7 is a side view of an illustrative embodiment of the aqueous humor drainage device of FIG. 3.

FIGS. 6 and 7 shows the dimensions of an exemplary embodiment of an aqueous humor drainage device 201 for use with the needle body 103 of FIG. 5. The tube 203 has a length of 8.5 mm. The duct 205 has a diameter of 0.07 mm. The outer surface 211 has a maximal cross sectional diameter (diameter D2) of 0.35 mm, which is less than the outer diameter D1 of the needle body 103. The tabs 213A, 213B are spaced by 4.5 mm from the distal end 209 of the tube 203 and spaced by 3 mm from the proximal end 207 of the tube 203. The tabs 213A, 213B are generally planar in form and lie in a common plane that extends transverse to the central axis of the tube 203. The tabs 213A, 213B are mirror images of one another reflected about the central axis of the tube 203 as shown. The planar form of the first and second tabs 213A, 213B has a maximal thickness on the order of 0.35 mm (i.e., the outer diameter D2 of the tube 203), a lengthwise dimension of 1 mm parallel to the central axis of the tube 203, and a maximal cross-sectional dimension between the edges 215A, 215B of 1.1 mm. In other designs, the maximal cross-sectional dimension between the edges 215A, 215B can be in the range between 0.9 mm and 1.5 mm. Such maximal cross-sectional dimension is significantly larger than the outer diameter D1 of 0.4 mm for the needle body 103 of FIG. 5.

Figure 8:
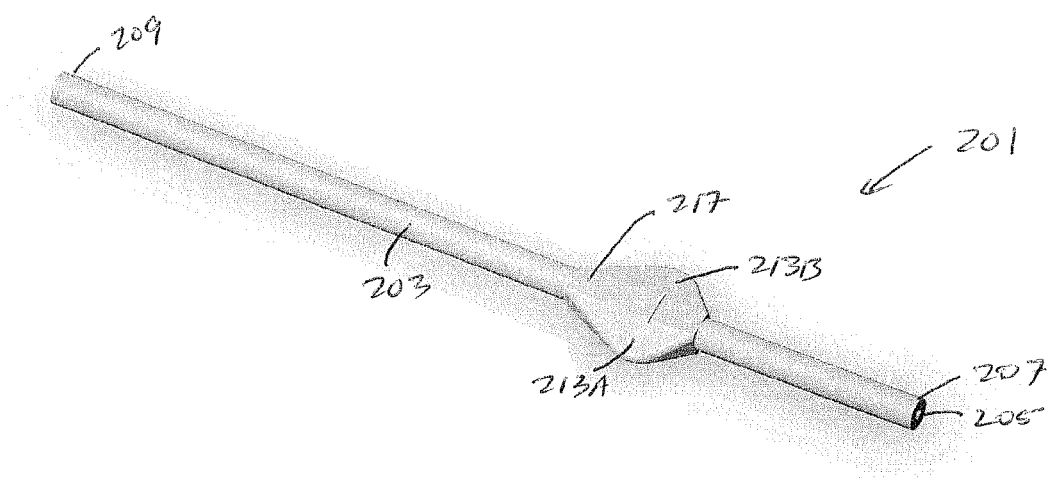
FIGS. 8-11 are perspective views of different embodiments of an aqueous humor drainage device.
Figure 9:
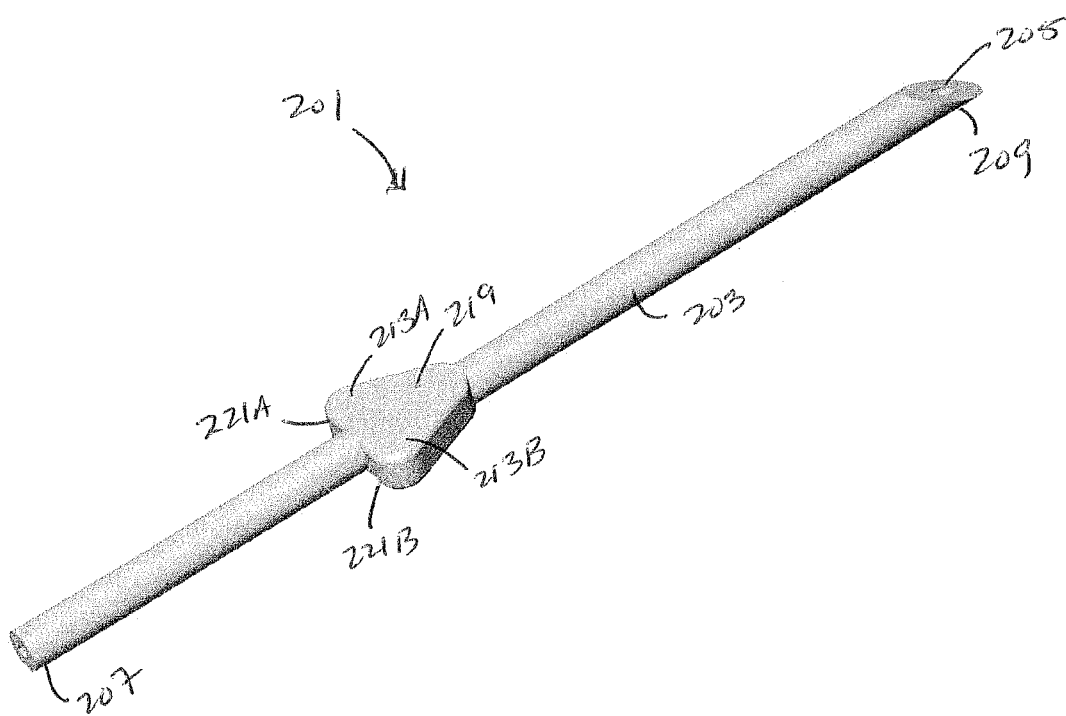
Figure 10:
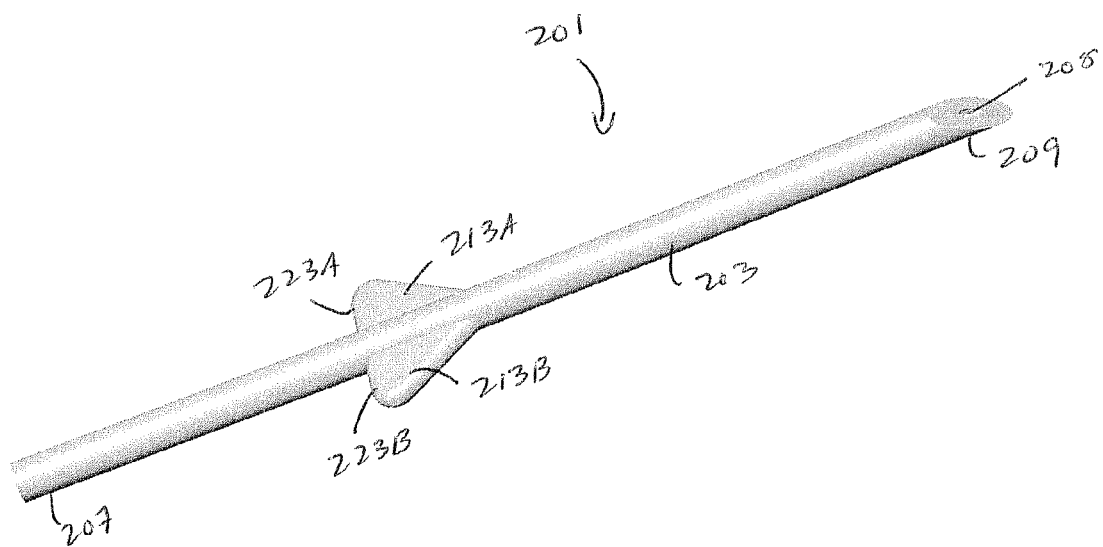
Figure 11:
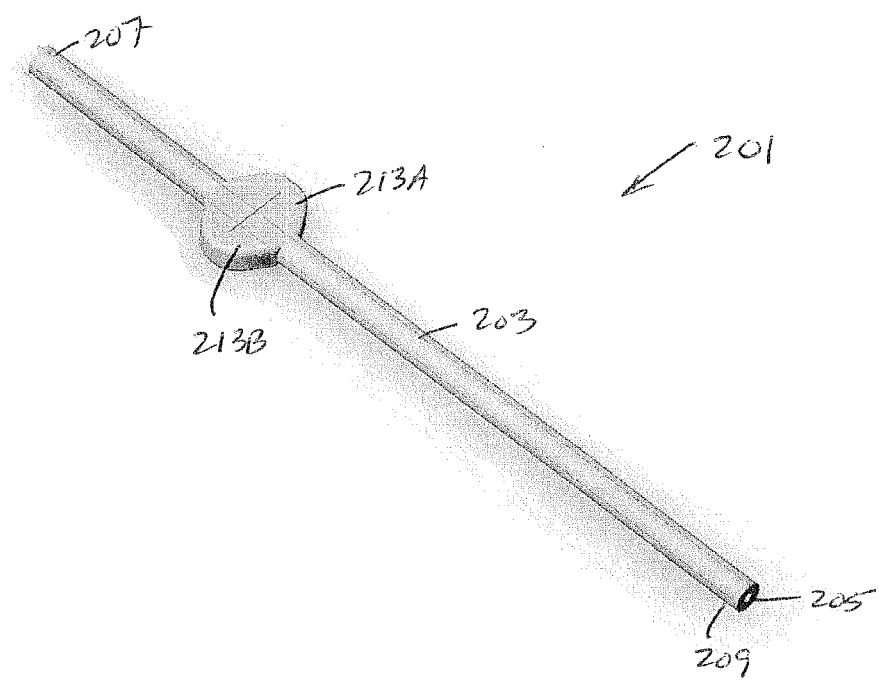
Figures 12A, 12B, 12C, 12D:
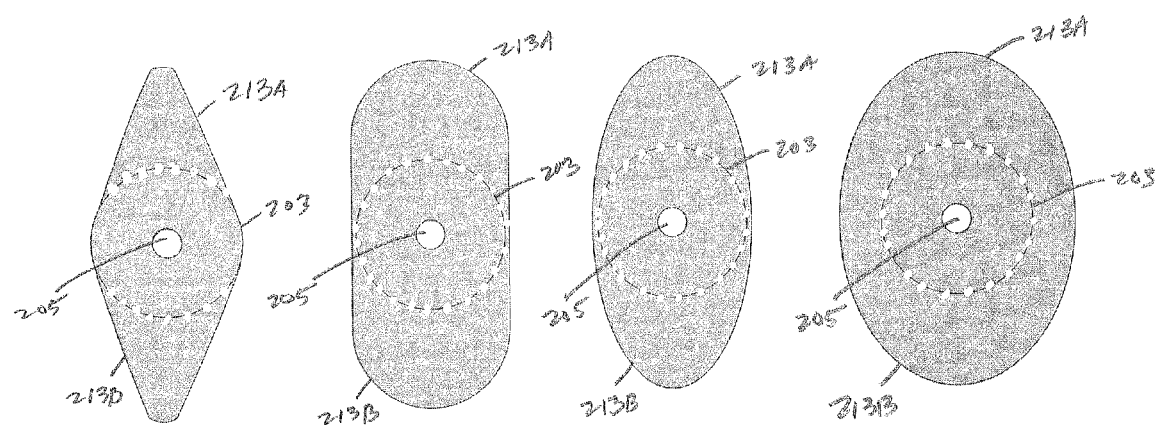
FIGS. 12A-12D are cross-sectional schematic views of views of different embodiments of an aqueous humor drainage device, showing the maximum dimension cross-sectional profiles of the sealing tabs of the respective embodiments.

FIGS. 8 to 14B illustrate alternate designs for the tabs of the implantable aqueous humor drainage device. In the design of FIG. 8, the tabs 213A1, 213B1 have a profile that tapers in the radial direction transverse to the central axis of the tube 203 where the tapered radial surfaces of the tabs extend from a flat feature 217. In the design of FIG. 9, the tabs 213A2, 213B2 are parts of a triangular wedged-shaped body 219 disposed along the lengthwise extent of the tube 203. The proximal walls 221A, 221B of the wedge-shaped body 219 are oriented transverse to the central axis of the tube 203, which is intended to aid in reducing migration of the tube 203 in the proximal direction out of the passage formed by the instrument 101. In the design of FIG. 10, the tabs 213A3, 213B3 have proximal walls 223A, 223B that are oriented transverse to the central axis of the tube 203, which is intended to aid in reducing migration of the tube 203 in the proximal direction out of the passage formed by the instrument 101. In the design of FIG. 11, the tabs 213A4, 213B4 each have a curved wedge-shaped form. In the design of FIG. 12A, the tabs 213A5, 213B5 and tube 203 define a cross-sectional profile of rhombus with radiused corners (in particular, the rhombus profile tapers in the radial direction transverse to and away from the central axis of the tube 203). The tapered surfaces of the tabs 213A5, 213B5 extend from the annular surface of the tube 203 as shown. In the design of FIG. 12B, the tabs 213A6, 213B6 define a cross-sectional profile of an oblong with semicircular ends as shown. Alternatively, the tabs 213A6, 213B6 can define a cross-sectional profile of an oblong with semielliptical ends. In the design of FIG. 12C, the tabs 213A7, 213B7 define a cross-sectional profile of an ellipse whose boundary is offset radially from and surrounds the annular surface of the tube 203. In the design of FIG. 12D, the tabs 213A8, 213B8 define a cross-sectional profile of a larger radius ellipse (as compared to the elliptical profile of FIG. 12C) whose boundary is offset radially from and surrounds the annular surface of the tube 203.

Figures 13A, 13B:
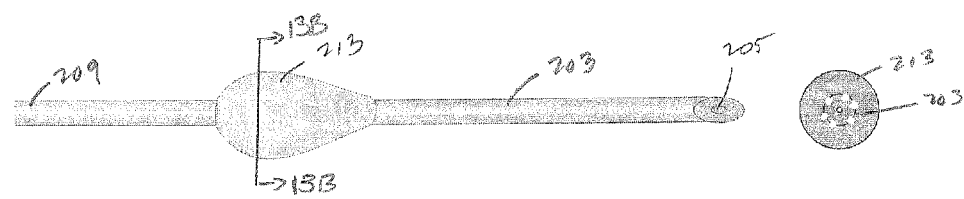
FIG. 13A is a top view of an embodiment of an aqueous humor drainage device.
FIG. 13B is a cross-sectional schematic view of the aqueous humor drainage device of FIG. 13A through the cross-section labeled 13B-13B, showing a circular cross-sectional profile of the sealing tabs of the aqueous humor drainage device.

In the design of FIGS. 13A and 13B, a cork-like tab 213' is provided that extends circumferentially beyond the annular surface of the tube 203. The cork-like tab 213' has a cross-sectional profile of a circle as is evident from the view of FIG. 13B.

Figures 14A, 14B:
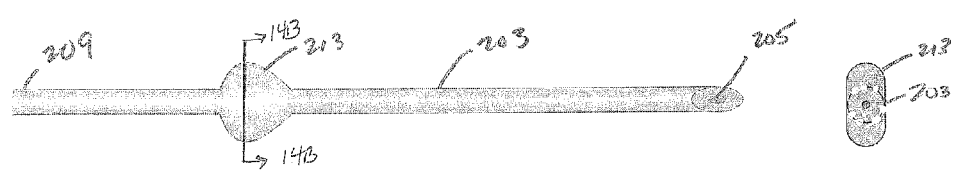
FIG. 14A is a top view of an embodiment of an aqueous humor drainage device.
FIG. 14B is a cross-sectional schematic view of the aqueous humor drainage device of FIG. 14A through the cross-section labeled 14B-14B, showing an oblong cross-sectional profile defined by the sealing tabs of the aqueous humor drainage device.

In the design of FIGS. 14A and 14B, a generally planar tab 213" is provided that extends circumferentially beyond the annular surface of the tube 203. The generally planar tab 213" has a cross-sectional oblong profile as is evident from the view of FIG. 14B.

The outer surface(s) of the tab(s) of the device 201 can be blunt with rounded features as shown, and thus avoid any sharp corners and edges. The blunt outer surface(s) of the tab(s) is particularly suited to forming a seal to the surrounding tissue as described herein.

In the design of FIG. 11, a slit 225 is formed in the tabs 213A, 213B in a manner such that the slit 225 transects the lumen 205 of the aqueous humor drainage device 205. The slit 225 is positioned proximal to that part of the tabs 213A, 213B that forms the seal to the surrounding tissue (i.e., the blunt exterior edges of the tabs 213A, 213B at their maximal radial distance with respect to the central axis of the tube 203). The purpose of the slit 225 is two-fold. First, the slit 225 can act as a pressure relief valve in the event the lumen 205 of the aqueous humor drainage device 205 becomes clogged downstream due to overgrowth of tissue in the bleb. The elastomeric nature of the aqueous humor drainage device 205 is such that as pressure builds up within the lumen 205, the slit 225 can deform into an open state where aqueous humor is released into the bleb thereby reducing pressure in the anterior chamber. The second advantage of the slit 225 is to deliberately accomplish the same purpose; that is to relieve pressure in the anterior chamber. In order to effectuate this release, the lumen 205 downstream from the slit 225 is sealed closed thereby forcing fluid to escape through the slit 225. The length and width of the slit 225 controls the pressure at which aqueous humor escapes and can be tailored to prevent hypotony. The aqueous humor escapes through the slit 225 and flows proximally in the space between the surrounding tissue and the outer surface of the proximal part of the tube 203. Fluid that escapes through the slit 225 will have its pressure dropped by both the narrow lumen 205 of the distal part of tube 203 as well as the slit 225. Periannular leakage of aqueous humor in the space between the surrounding tissue and the outer surface of the distal part of the tube 203 is blocked by the seal formed by the tabs 213A, 213B. More specifically, the blunt exterior edges of the tabs 213A, 213B at their maximal radial offset with respect to the central axis of the tube 203 forms a seal with the surrounding tissue that blocks such periannular leakage of aqueous humors.

The aqueous humor drainage device 201 can be formed of a homogenous polymeric material. In one embodiment, the homogenous polymeric material is a polyolefinic copolymer material having a triblock polymer backbone comprising polystyrene-polyisobutylene-polystyrene, which is herein referred to as "SIBS". SIBS can also be referred to as poly(styrene-b-isobutylene-b-styrene) where b stands for "block". High molecular weight polyisobutylene (PIB) is a soft elastomeric material with a Shore hardness of approximately 10 A to 30 A. When copolymerized with polystyrene, it can be made at hardnesses ranging up to the hardness of polystyrene, which has a Shore hardness of 100 D. Thus, depending on the relative amounts of styrene and isobutylene, the SIBS material can have a range of hardnesses from as soft as Shore 10 A to as hard as Shore 100 D. In this manner, the SIBS material can be adapted to have the desired elastomeric and hardness qualities. In the preferred embodiment, the SIBS material of the aqueous humor drainage device tube 201 has a hardness less than Shore 50 A and greater than Shore 20 A. Details of the SIBS material is set forth in U.S. Pat. Nos. 5,741,331; 6,102,939; 6,197,240; 6,545,097, which are hereby incorporated by reference in their entirety. The SIBS material of the aqueous humor drainage device 201 may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between 16 mole % and 30 mole % and most preferably between 20 mole % and 27 mole %. The styrene and isobutylene copolymer materials are preferably copolymerized in solvents.

Alternative glassy segments to the aforementioned styrene can be used to realize the aqueous humor drainage device 201. The glassy segment provides a hardener component for the elastomeric polyisobutylene. The glassy segment preferably does not contain any cleavable group which will release in the presence of body fluid inside the human eye and cause toxic side effects and cell encapsulation. The glassy segment can be a vinyl aromatic polymer (such as styrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Such materials have a general structure:

BAB or ABA (linear triblock),
B(AB)n or a(BA)n (linear alternating block), or
X-(AB)n or X-(BA)n (includes diblock, triblock and other radial block copolymers), where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers. In addition to the glassy segments, crosslinkers can be incorporated into the polymer to provide a thermal-set version of SIBS. Exemplary polymers incorporating these crosslinkers are described in detail in U.S. Patent Publication 20090124773, herein incorporated by reference in its entirety. These materials collectively belong to the polymeric material referred to herein as SIBS material.

Other polymeric materials can be used to provide aqueous drainage device 201 according to this invention. Exemplary materials are flexible materials that can conform to the surface of the eye and include but are not limited to silicone rubber, polyolefins (butyl rubber, polybutadiene, styrene-ethylene-propylene-butadiene, polyethylene, polypropylene, etc.) polyurethane (polyether urethanes, polycarbonate urethanes, polyurethanes containing polyisobutylene or other polyolefin soft segments, etc.); acrylics (polyacrylates, poly(2-hydroxyethylmethacrylate), etc.), fluoropolymers (PTFE, ePTFE, fluorosilicones, poly(—CH2—CF2)-, etc.), polyamides, hydrogels, biological based structures such as those comprised of collagen, elastin, etc.; and blends of all the above materials as well as soft foams and porous polymer materials can be used to realize the aqueous humor drainage device 201. The polymeric material should be biocompatible and biostable within the ocular environment.

The entire aqueous humor drainage device 201 can be formed as a unitary part by molding the polymeric material. It is also contemplated that the polymeric material of the tabs 213A, 213B can be different from the polymeric material of the tube 203. This can be accomplished by insert molding techniques or other suitable thermoplastic forming techniques. The hardnesses of the tabs 213A, 213B can be the same as the tube 203, or they can differ from the tube 203. In one embodiment, the hardnesses of the tabs 213A, 213B are within the range between Shore 30 A and Shore 80 A.

Figure 15:
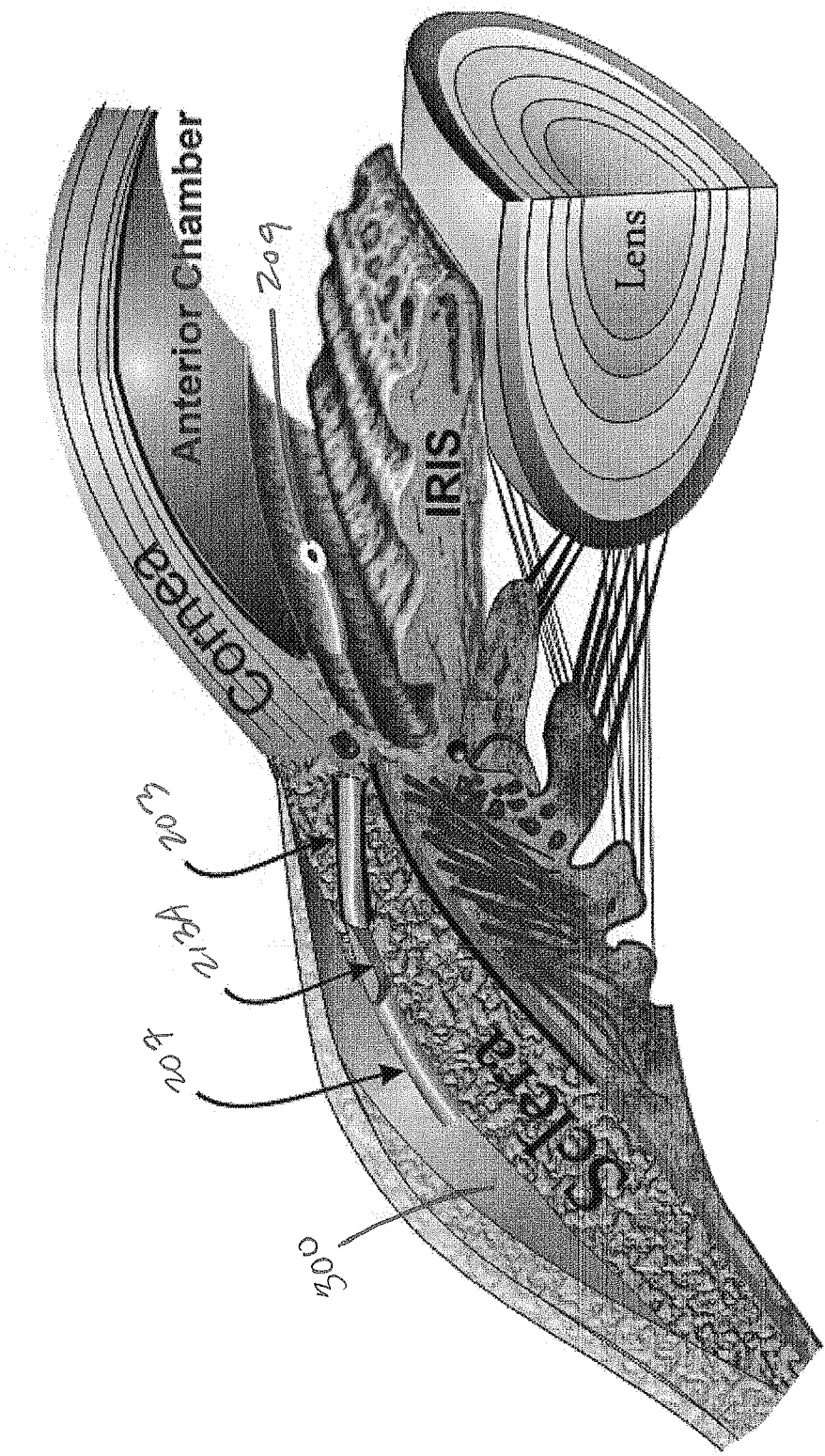
FIG. 15 is an illustration showing the aqueous humor drainage device of FIG. 3 implanted into the eye to shunt aqueous humor from the anterior chamber to a space between Tenon's membrane and the sclera of the eye.

Turning now to FIG. 15, there is shown the aqueous humor drainage device 201 implanted such that its distal end 209 is positioned within the anterior chamber 20 of the eye and its proximal end 207 is positioned in a pouch 300 formed between Tenon's membrane 36 and the sclera 26 (FIG. 1). The pouch 300 defines a closed space between Tenon's membrane 36 and the sclera 26 (FIG. 1). The duct 205 of the aqueous humor drainage device 201 shunts aqueous humor from the anterior chamber 20 to the pouch 300, which forms a shallow bleb. Aqueous humor is absorbed into the adjacent tissue and ends up in the venous system in the eye or in the tear film or simply evaporates from the outside of the conjunctiva once it reaches such.

The pouch 300 can extend rearward from a location at or near the limbus to the posterior portion of the globe of the eye near or past the equator of the eye. The pouch 300 can be defined by making an incision through the conjunctiva or Tenon's membrane 36 to the surface of the sclera and then dissecting and separating Tenon's membrane 36 from the sclera 26 (FIG. 1) over the area of the pouch 300. If the hinge from the pouch is in the fornix of the eye, this type of pouch is known as a fornix-based pouch. If the hinge is at the limbus and the incision in the fornix, this type of pouch is known as a limbus-based pouch. The distal end 209 of the aqueous humor drainage device 201 is inserted through a needle-formed passage through the angle 28 to the anterior chamber 20 of the eye. The device 201 is advanced further into the passage such that tabs 213A, 213B (only tab 213A is shown in FIG. 15) are positioned within the passage. The dimensions of the tabs 213A, 213B cause the surrounding tissue to directly contact the tabs 213A, 213B in order to form a seal between the surrounding tissue and the tabs 213A, 213B. The seal surrounds the entire circumferential perimeter of the device defined by the tabs 2213A, 213B and prevents leakage of aqueous humor through the space between the tube 203 and the surrounding tissue. The tabs 213A, 213B can deform in the passage as they are inserted into the passage in response to forces applied by the surrounding tissue, and/or the surrounding tissue can deform (by stretching/thinning) as the tabs 213A, 213B are inserted into the passage. Such deformation is controlled by the maximal cross-sectional dimension of the tabs 213A, 213B relative to the cross-sectional dimension of the passage (as formed by the needle body 103) as well as the hardness of the material of the tabs 213A, 213B. The tabs 213A, 213B also act to fix the tube 203 in place in the passage and minimize migration of the tube 203 in both the proximal and distal directions. After proper positioning of the device 201, the pouch 300 is closed. A sponge, blotting paper or other suitable carrier loaded with an anti-proliferative agent can be placed within the pouch 300 before it is closed. The anti-proliferative agent may be, for example, mitomycin C or 5-Fluorouracil or other antimetabolites or other suitable drug(s) or compound(s) that releases immediately or over time and functions to minimize fibrosis of the conjuctiva-sclera to Tenon's membrane, thereby maintaining the structure of the pouch 300 over an extended period of time. Alternatively, a collagen sponge or other space-filler structure or fluid can be placed in the pouch to prevent healing of the conjunctiva/Tenon's membrane to the sclera. Aqueous humor flows from the anterior chamber 20 through the duct 205 of the device 203 and into the sealed pouch 300. The sealed pouch 300 prevents bacteria from entering the device 201 and infecting the eye. Aqueous humor exiting the device 201 and entering the sealed pouch 300 creates a very shallow bleb. The bleb fluid may filter through the conjunctiva 30 (FIG. 1) into the tears or evaporate therefrom, and the fluid may be absorbed through the lymphatic system and capillaries that interpenetrate the conjunctiva 30 (FIG. 1). A fraction of the aqueous humor contained in the bleb may potentially seep through the permeable sclera 26 and be absorbed by the choroidal capillaries.

The aqueous humor drainage device 201 can be implanted into the position shown in FIG. 15 utilizing the following method. The pouch 300 is made by dissecting the conjunctiva 30 at the limbus 32 in an incision area that is less than one quadrant using miniature scissors (Vannas scissors or similar) and dissecting and separating Tenon's membrane 36 from the sclera 26 over a few millimeters (a fornix-based flap). Then, holding the edge of the pouch 300 at its center with toothed forceps, the closed tips of a pair of blunt scissors (e.g. Westcott or similar) are slowly pushed downward toward the eye equator and opened up to separate (delaminate) Tenon's membrane 36 from the sclera 26. The scissors are again closed; its tips pushed further forward and reopened to separate a larger area of Tenon's membrane 36. The process is repeated until the tips of the scissors are 17 to 20 mm away from the limbus 32. The pouch 300 thusly created is larger at the equatorial base than at the limbal entry.

The pouch 300 is formed adjacent to the limbus 32. A mark, centered in the middle of the conjunctival opening is made 2-3 mm behind the limbus' edge using a blunt caliper. A tissue ink can be used on the tip of the caliper to increase contrast of the tissue mark. A hand-held instrument 101 with a needle body 103 (FIG. 1) is prepared and the tip of the needle body 103 is positioned at the mark made on the sclera. A surgical passage is fashioned to connect the scleral outer wall to the anterior chamber by pushing the needle body 103 in a plane such that the tip of the needle body 103 enters the eye through the angle 28 into the anterior chamber 20. In this manner, the surgical passage passes through the conjuctiva-sclera in the vicinity of the angle 28 and into the anterior chamber 20. The instrument 101 may be a syringe that holds a pharmacological solution, such as epinephrine or lidocain. The surgeon may elect to dispense the solution from the syringe into the anterior chamber 20 after introduction of the distal end of the syringe needle body 103 into the anterior chamber 20. After waiting for some time (e.g., a few seconds), the needle body 103 is slowly retracted. The aqueous humor drainage device 201 is inserted into the surgical passage into the position shown in FIG. 15 whereby the distal end 209 exits into the anterior chamber 20 of the eye and the tabs 213A, 213B are positioned within the surgical passage. Before introducing the device 201 into the surgical passage, the proximal end of the surgical passage can be enlarged at the scleral surface by means of a stab incision with a sharp knife (such as the knife of FIGS. 18A and 18B as described below) or by cutting the entrance to the sclera with the sharp edge of the needle body 103 as it is withdrawn. This stab incision can assist in the introduction of the tabs 213A, 213B of the device 201 into the surgical passage. Alternatively, prior to making the surgical passage, the sharp knife is used to make a shallow slit or stab-wound into the sclera. A needle is then inserted into the slit and the surgical passage formed under the limbus. The tabs 213A, 213B are then tucked into the stab wound as described above. The dimensions of the tabs 213A, 213B cause the surrounding ocular tissue of the surgical passage to directly contact the tabs 213A, 213B in order to form a seal between the surrounding ocular tissue and the tabs 213A, 213B. The seal surrounds the entire circumferential perimeter of the device defined by the tabs 213A, 213B and prevents leakage of aqueous humor through the space between the tube 203 and the surrounding ocular tissue of the surgical passage. The proximal end 207 of the tube 203 is positioned in the pouch 300 as shown in FIG. 15. The aqueous humor drainage device 201 can be deployed from an inserter device similar to that described in U.S. Pat. Nos. 7,431,709, 7,594,899, and 7,837,644 with one or two slots that accommodate the tabs 213A, 213B of the device 201. Alternatively, the aqueous humor drainage device 201 can be inserted into the passage using a stylet 301 and/or a trocar device 350 (or 410) as described below. The pouch 300 is then closed with sutures 304. Instead of sutures, bipolar diathermy coagulation, laser welding or adhesives, such as cyanoacrylate, fibrin glue, etc. can be used to close the pouch 300. Further, a trocar can be used to facilitate placement of the aqueous humor drainage device through the needle passage.

To minimize inflammation as well as reduce surgical time, the pouch 300 can also be created by dissection of the conjunctiva at the limbus and, starting at one edge of the dissection, cutting the conjuctival tissue posteriorly for about 3 mm, thus creating a flap door. After forming the surgical passage into the exposed sclera and through to the anterior chamber, the device 201 is positioned in the surgical passage with the proximal end of the device in the pouch 300 as shown in FIG. 12. The freed edge of the conjunctiva 30 is then juxtaposed about 2 mm past its original position and held taut with a single suture, or a single laser weld, or a single-point bipolar diathermy coagulation, or with a single dot of adhesive. The edge of the conjunctiva 30 along the limbus 32 is never treated, but left intact to prevent tissue necrosis that engenders fibrosis. The cornea-limbal epithelium cells will rapidly recover the wound edge (1 hour or less), sealing the conjunctival limbus.

A sponge, blotting paper or other suitable carrier loaded with one or more therapeutic agents can be placed within the pouch 300 before it is closed. Such therapeutic agent(s) release over time and minimizes fibrosis of Tenon's membrane to the sclera, thereby preventing re-lamination and closure of the bleb space (the interior space of the closed pouch 300 that surrounds the proximal end 207 of the tube 203). The therapeutic agents(s) can include cytostatic agents (i.e., anti-proliferation agents that prevent or delay cell division, for example, by inhibiting replication of DNA, and/or by inhibiting spindle fiber formation, and/or by inhibiting cell migration) or other agents that minimize fibrosis or blood clots. Examples of such therapeutic agents are described below.

FIG. 16 shows the aqueous humor drainage device 201 with a stylet 301 that is removably inserted into the lumen 205 of the proximal portion 209 of the device 201 to aid in the insertion of the device 201 into the needle-formed passage. The proximal end of the stylet 301 is bent in a pig-tail configuration 302 to enable the surgeon to grip the stylet 301 and remove it from the lumen 205 of the aqueous humor drainage device 201 once it is in place. FIG. 17 shows another embodiment of the stylet 301 where a larger tube 303 is crimped onto the proximal end of the stylet to facilitate gripping and removal.

FIGS. 18A and 18B show a hand-held knife 340 that can be used to make the stab wound in the sclera to further secure the elements of the aqueous humor drainage device 201 in the sclera. The Diameter "a" of the knife edge 341 is less than the maximal cross-sectional diameter of the tabs 213A, 213B of the device 201 in order to enable a snug fit of the tabs 213A, 213B into the stab wound. The length b of the knife edge 341 can be approximately the same dimension as the dimension a.

FIG. 18C shows an embodiment of a hand-held instrument 342 that includes a distal needle body 343 extending from a flat blade portion with cutting surfaces 344A, 344B. The needle body 343 creates the passage leading through the sclera and the cutting surfaces 344A, 344B create a widened stab wound in the sclera in one motion of the surgeon's hand.

When the needle body is removed from the needle-formed passage, the needle passage can at times become oval (or collagen fibers cross the passage or there is a bend in the passage), which results in difficulty placing the aqueous humor drainage device 201 through the passage. In order to facilitate placement of the aqueous humor drainage device 201 into the needle-formed passage through the sclera, a trocar 350 which includes a conduit 352 with a skived slot 351 (FIG. 19) can be provided. The conduit 352 is sized to receive the needle body 103 as well as the tube 203 of the aqueous humor drainage device 201. The trocar 350 is placed over the needle body 103 to provide the assembly 360 shown in FIG. 20A. FIGS. 20B to 20E illustrate the function of the trocar 350. The assembly 360 is inserted into the needle-formed passage through the sclera 400 as is shown in FIG. 20B. The needle body 103 is then removed from the assembly leaving trocar 350 in place as shown in FIG. 20C. The aqueous humor drainage device 201 is then fed through the trocar 350 as shown in FIG. 20D. The trocar 350 is then removed leaving the aqueous humor drainage device 201 behind inside the needle-formed passage as shown in FIG. 20E. The elastic nature of the tube 203 of the device 201 allows the tube 203 to bend and deform such that it passes through the slot 351 of the trocar 350 as the trocar 305 is removed. The position of the aqueous humor drainage device 201 within the passage can then be adjusted by the surgeon (for example, by further inserting the device 201 into the passage) such that the tabs 213A, 213B interface to the tissue wall of the passage and provide a seal between the tissue and the device 201. In this position, the tabs 213A, 213B also act to fixate the device in the passage.

Figure 20A:
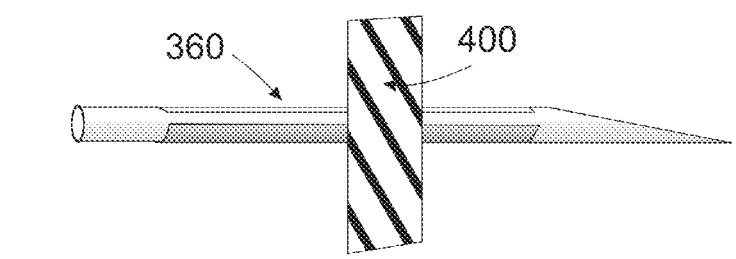
FIGS. 20A to 20E illustrate the function of the trocar device of FIG. 19 in an exemplary surgical method.
Figure 20B:
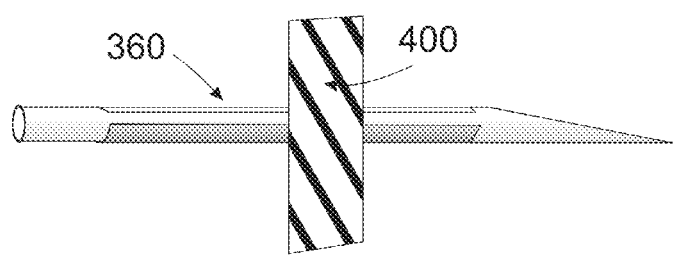
Figure 20C:
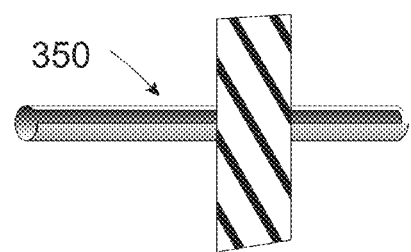
Figure 20D:
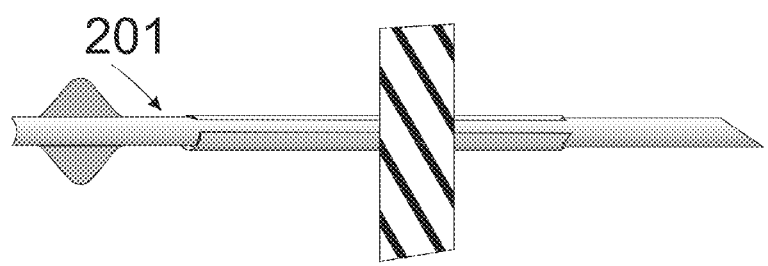
Figure 20E:
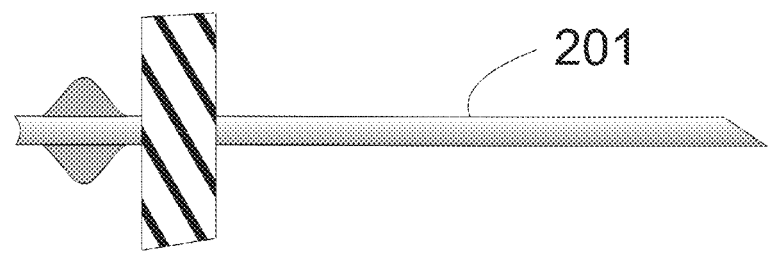
Figure 21:
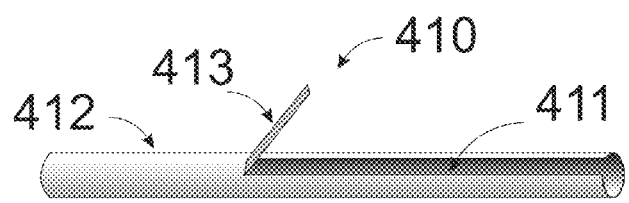
FIG. 21 is a side view of an alternate embodiment of a trocar device used in a surgical method for treating elevated intraocular pressure, the trocar device inserted into a passage through tissue and in communication with the anterior chamber of the eye, and the trocar device receiving the tube of an aqueous humor drainage device for insertion of the tube of the aqueous humor drainage device into the passage.
Figure 22A:
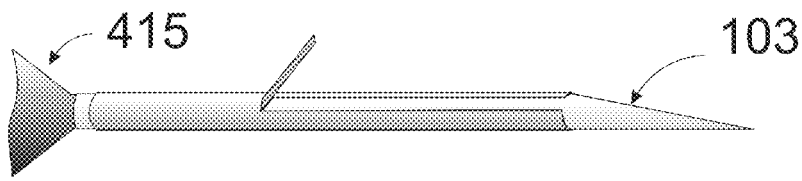
FIGS. 22A to 22D illustrate the function of the trocar device of FIG. 21 in an exemplary surgical method.
Figure 22B:
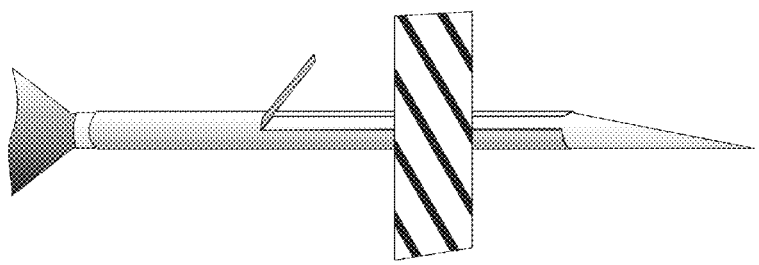
Figure 22C:
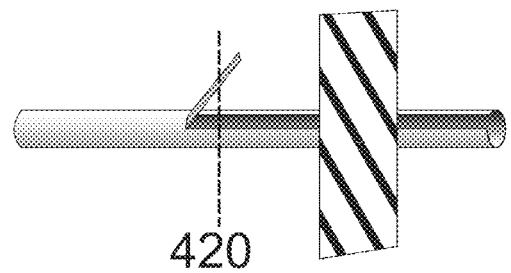
Figure 22D:
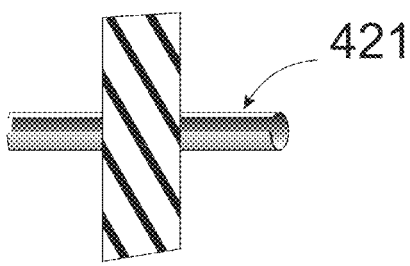

FIG. 21 shows another embodiment of a trocar 410, which includes a conduit 412 with a slot 411 which is skived partway along the conduit 412. A section of the lid of the skived slot (e.g., tab 413) remains integral with the tube as is shown. The conduit 412 is sized to receive the needle body 103 as well as the tube 203 of the aqueous humor drainage device 201. The trocar 410 is placed over the needle body 103 with the hub 415 butting against the proximal end of conduit 412 to provide the assembly shown in FIG. 22A. FIGS. 22B to 22D illustrate the function of the trocar 410. The assembly is inserted into the needle-formed passage through the sclera 400 as is shown in FIG. 22B. The abutment of conduit 412 to the hub 415 prevents the trocar 410 from slipping backward on the needle body as it is inserted through tissue. The needle body 103 is removed from trocar 410 as shown in FIG. 22C, which is facilitated by gripping tab 413 with a forceps as needle 103 is pulled out of trocar 410. Once the needle body 102 is removed, the trocar 410 is cut at line 420 (for example, with scissors) and the proximal portion of the conduit 412 with tab 413 is discarded as shown in FIG. 22D. The aqueous humor drainage device 201 is then fed through the remaining trocar portion 421 into the needle-formed passage in a manner similar to the method described above in conjunction with FIG. 20D. The trocar portion 421 is then removed leaving the aqueous humor drainage device 201 behind inside the needle-formed passage as shown in FIG. 20E. The elastic nature of the tube 203 of the device 201 allows the tube 203 to bend and deform such that it passes through the slot 411 of the trocar portion 421 as the trocar portion 421 is removed. The position of the aqueous humor drainage device 201 within the passage can then adjusted by the surgeon (for example, by further inserting the device 201 into the passage) such that the tabs 213A, 213B interface to the tissue wall of the passage and provide a seal between the tissue and the device 201. In this position, the tabs 213A, 213B also act to fixate the device in the passage.

Another embodiment contemplated by this invention is to first form the needle tract under the limbus with needle 103, then pre-load tube 203 of the aqueous humor drainage device 201 into trocar 350 or 410 and then push the assembly through the needle tract. The trocar is then removed from the needle tract as explained above.

Figure 19:
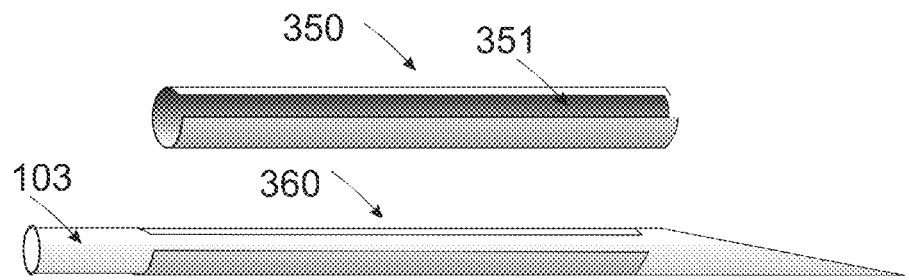
FIG. 19 is a side view of an embodiment of a trocar device used in a surgical method for treating elevated intraocular pressure, the trocar device inserted into a passage through tissue and in communication with the anterior chamber of the eye, and the trocar device receiving the tube of an aqueous humor drainage device for insertion of the tube of the aqueous humor drainage device into the passage.

The trocars of FIGS. 19 and 21 can be made from a stiff thin material preferably polyimide. Other materials that may function in this capacity are PEEK, PEEKEK, polyurethane, polypropylene, high molecular weight polyethylene, Nylon, fluoropolymers, etc. Alternatively, the material forming the trocars can be made from metal (preferably well-known metals used in medical devices such as stainless steel, titanium, Nitinol, etc.). The main requirement is that when the trocar is inserted through tissue that it not buckle. The wall thickness of the trocar should be between 0.0002" and 0.003"; preferably between 0.001 and 0.003". The inner diameter of the trocar should be equal to or larger than the diameter of the needle body 103; that is, if inserted over a needle, or equal to or larger than the flexible tube 102 if the trocar is pre-loaded with the aqueous drainage device.

The polymeric aqueous humor drainage device 201 (or parts thereof) can be loaded with one or more therapeutic agents that release over time and minimize fibrosis of the Tenon's membrane to the sclera, thereby preventing re-lamination and closing of the bleb space. The therapeutic agents(s) loaded into the device 100 can include cytostatic agents (i.e., anti-proliferation agents that prevent or delay cell division, for example, by inhibiting replication of DNA, and/or by inhibiting spindle fiber formation, and/or by inhibiting cell migration) or other agents that minimize fibrosis or blood clots. Examples of such therapeutic agents follow.

Representative examples of therapeutic agents include the following: Visudyne, Lucentis (rhuFab V2 AMD), Combretastatin A4 Prodrug, SnET2, H8, VEGF Trap, Candy, LS 11 (Taporfin Sodium), AdPEDF, RetinoStat, Integrin, Panzem, Retaane, Anecortave Acetate, VEGFR-1 mRNA, ARGENT cell-signaling technology, Angiotensin II Inhibitor, Accutane for Blindness, Macugen (PEGylated aptamer), PTAMD, Optrin, AK-1003, NX 1838, Antagonists of avb3 and 5, Neovastat, Eos 200-F and any other VEGF inhibitor.

Other therapeutic agents can be used such as: mitomycin C, 5-fluorouracil, corticosteroids (corticosteroid triamcinolone acetonide is most common), modified toxins, methotrexate, adriamycin, radionuclides (e.g., such as disclosed in U.S. Pat. No. 4,897,255, herein incorporated by reference in it entirety), protein kinase inhibitors (including staurosporin, which is a protein kinase C inhibitor, as well as a diindoloalkaloids and stimulators of the production or activation of TGF-beta, including tamoxifen and derivatives of functional equivalents, e.g., plasmin, heparin, compounds capable of reducing the level or inactivating the lipoprotein Lp(a) or the glycoprotein apolipoprotein(a) thereof), nitric oxide releasing compounds (e.g., nitroglycerin) or analogs or functional equivalents thereof, paclitaxel or analogs or functional equivalents thereof (e.g., taxotere or an agent based on Taxol®, whose active ingredient is paclitaxel), inhibitors of specific enzymes (such as the nuclear enzyme DNA topoisomerase II and DAN polymerase, RNA polyermase, adenl guanyl cyclase), superoxide dismutase inhibitors, terminal deoxynucleotidyl-transferas, reverse transcriptase, antisense oligonucleotides that suppress cell proliferation, angiogenesis inhibitors (e.g., endostatin, angiostatin and squalamine), rapamycin, everolimus, zotarolimus, cerivastatin, and flavopiridol and suramin and the like.

Other examples of therapeutic agents include the following: peptidic or mimetic inhibitors, such as antagonists, agonists, or competitive or non-competitive inhibitors of cellular factors that may trigger proliferation of cells or pericytes (e.g., cytokines (for example, interleukins such as IL-1), growth factors (for example, PDGF, TGF-alpha or -beta, tumor necrosis factor, smooth muscle- and endothelioal-derived growth factors such as endothelin or FGF), homing receptors (for example, for platelets or leukocytes), and extracellular matrix receptors (for example, integrins).

Representative examples of useful therapeutic agents in the category of agents that address cell proliferation include: subfragments of heparin, triazolopyrimidine (for example, trapidil, which is a PDGF antagonist), lovastatin; and prostaglandins E1 or I2.

Several of the above and numerous additional therapeutic agents appropriate for the practice of the present invention are disclosed in U.S. Pat. Nos. 5,733,925 and 6,545,097, both of which are herein incorporated by reference in their entirety.

If desired, a therapeutic agent of interest can be provided at the same time as the polymer from which the device 201 is realized, for example, by adding it to a polymer melt during thermoplastic processing or by adding it to a polymer solution during solvent-based processing. Alternatively, a therapeutic agent can be provided after formation of the device or device portion. As an example of these embodiments, the therapeutic agent can be dissolved in a solvent that is compatible with both the device polymer and the therapeutic agent. Preferably, the device polymer is at most only slightly soluble in this solvent. Subsequently, the solution is contacted with the device or device portion such that the therapeutic agent is loaded (e.g., by leaching/diffusion) into the copolymer. For this purpose, the device or device portion can be immersed or dipped into the solution, the solution can be applied to the device or component, for example, by spraying, printing dip coating, immersing in a fluidized bed and so forth. The device or component can subsequently be dried, with the therapeutic agent remaining therein.

In another alternative, the therapeutic agent may be provided within a matrix comprising the polymer of the device 201. The therapeutic agent can also be covalently bonded, hydrogen bonded, or electrostatically bound to the polymer of the device 201. As specific examples, nitric oxide releasing functional groups such as S-nitroso-thiols can be provided in connection with the polymer, or the polymer can be provided with charged functional groups to attach therapeutic groups with oppositely charged functionalities.

In yet another alternative embodiment, the therapeutic agent can be precipitated onto one or more surfaces of the device 201 (or device portion). These one or more surface(s) can be subsequently covered with a coating of polymer (with or without additional therapeutic agent) as described above.

Hence, for purposes herein, when it is stated herein that the polymer is "loaded" with therapeutic agent, it is meant that the therapeutic agent is associated with the polymer in a fashion like those discussed above or in a related fashion.

In some instances a binder may be useful for adhesion to a substrate. Examples of materials appropriate for binders in connection with the present invention include silanes, titanates, isocyanates, carboxyls, amides, amines, acrylates hydroxyls, and epoxides, including specific polymers such as EVA, polyisobutylene, natural rubbers, polyurethanes, siloxane coupling agents, ethylene and propylene oxides.

It also may be useful to coat the polymer of the device 201 (which may or may not contain a therapeutic agent) with an additional polymer layer (which may or may not contain a therapeutic agent). This layer may serve, for example, as a boundary layer to retard diffusion of the therapeutic agent and prevent a burst phenomenon whereby much of the agent is released immediately upon exposure of the device or device portion to the implant site. The material constituting the coating, or boundary layer, may or may not be the same polymer as the loaded polymer. For example, the barrier layer may also be a polymer or small molecule from the following classes: polycarboxylic acids, including polyacrylic acid; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA (ethylene-vinyl acetate copolymer); polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; polypeptides, including proteins; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; and hyaluronic acid.

Copolymers and mixtures of the above are also contemplated.

It is also possible to form the aqueous humor drainage device 201 (or device portion) with blends by adding one or more of the above or other polymers to a block copolymer. Examples include the following:

Blends can be formed with homopolymers that are miscible with one of the block copolymer phases. For example, polyphenylene oxide is miscible with the styrene blocks of polystyrene-polyisobutylene-polystyrene copolymer. This should increase the strength of a molded part or coating made from polystyrene-polyisobutylene-polystyrene copolymer and polyphenylene oxide.

Blends can be made with added polymers or other copolymers that are not completely miscible with the blocks of the block copolymer. The added polymer or copolymer may be advantageous, for example, in that it is compatible with another therapeutic agent, or it may alter the release rate of the therapeutic agent from the block copolymer (e.g., polystyrene-polyisobutylene-polystyrene copolymer).

Blends can be made with a component such as sugar (see list above) that can be leached from the device 201 (or device portion), rendering the device or device component more porous and controlling the release rate through the porous structure.

The release rate of therapeutic agent from the therapeutic-agent-loaded polymers of the present invention can be varied in a number of ways. Examples include:

Varying the molecular weight of the block copolymers.

Varying the specific constituents selected for the elastomeric and thermoplastic portions of the block copolymers and the relative amounts of these constituents.

Varying the type and relative amounts of solvents used in processing the block copolymers.

Varying the porosity of the block copolymers.

Providing a boundary layer over the block copolymer.

Blending the block copolymer with other polymers or copolymers.

Moreover, although it is seemingly desirable to provide control over the release of the therapeutic agent (e.g., as a fast release (hours) or as a slow release (weeks)), it may not be necessary to control the release of the therapeutic agent. In such embodiments, one or more of the therapeutic drug agents described herein (e.g., an antiproliferative agent derived from mitomycin C or 5-fluorouracil) may be injected into the pouch 300 at the time of surgery.

There have been described and illustrated herein several embodiments of glaucoma implant devices, kits and methods that divert aqueous humor from the anterior chamber of the eye and surgical methods associated therewith. While particular embodiments of the invention have been described, it is not intended that the invention be limited thereto, as it is intended that the invention be as broad in scope as the art will allow and that the specification be read likewise.

Thus, while particular methods of manufacture have been disclosed, it will be understood that other manufacture methods can be used. For example, because the copolymer materials described herein have a thermoplastic character, a variety of standard thermoplastic processing techniques can be used to for the devices described herein. Such techniques include compression molding, injection molding, blow molding, spinning, vacuum forming and calendaring, and extrusion into tubes and the like. Such devices can also be made using solvent-based techniques involving solvent casting, spin coating, solvent spraying, dipping, fiber forming, ink jet techniques and the like. Also, while it is preferred that the aqueous humor drainage device be realized by a simple tubular structure, it will be recognized that adaptations may be made of such structures. For example, other duct forming structures and shapes can be used. In another example, the device may include holes through the side wall of the tubular structure. In another example, the tubular structure may include multiple lumens therein. Also, while it is preferred that the aqueous humor drainage device be realized by simple planar tab structures, it will be recognized that adaptations may be made of such structures. It will therefore be appreciated by those skilled in the art that yet other modifications could be made to the provided invention without deviating from its spirit and scope as claimed.

What is claimed is:

1. A kit for surgical treatment of elevated ocular pressure within the anterior chamber of the eye, the kit comprising:
an instrument having a needle body for insertion through tissue to define a tissue passage connecting to the anterior chamber, wherein said needle body has a first maximal cross-sectional dimension along its length; and
an aqueous humor drainage device consisting of a flexible tube and a tissue seal extending radially outward from said tube in at least two opposing directions,
wherein said tube defines a duct for diverting aqueous humor from the anterior chamber, said tube having a central axis and having a proximal portion defining a cylindrical outer surface and a distal portion defining a cylindrical outer surface, the cylindrical outer surfaces of the proximal portion and the distal portion having a second maximal cross-sectional dimension that is less than said first maximal cross-sectional dimension, and
wherein said seal is spaced apart from and intermediate the cylindrical outer surfaces of said proximal and distal portions of said tube, said seal extending radially outward beyond the cylindrical outer surfaces of said proximal and distal portions of said tube, and said seal having a third maximal cross-sectional dimension that is greater than said first maximal cross-sectional dimension and structured in order to form a seal between the tissue passage and said seal.

2. A kit according to claim 1, wherein:
said seal has a proximal surface and a distal surface, said distal surface having a tapered profile that extends away from the distal portion of said tube toward the proximal portion of said tube.

3. A kit according to claim 2, wherein:
said third maximal cross-sectional dimension of said seal is defined by at least one blunt surface formed between the proximal and distal surfaces of said seal.

4. A kit according to claim 1, wherein:
said seal is dimensioned to fit entirely within the scleral tissue.

5. A kit according to claim 1, wherein:
said opposing directions extend transverse to the central axis of the tube.

6. A kit according to claim 1, wherein:
said seal has a circular cross-section in a direction transverse to the central axis of the tube.

7. A kit according to claim 1, wherein:
said seal has a rhomboid cross-section in a direction transverse to the central axis of the tube.

8. A kit according to claim 1, wherein:
said seal has an oblong cross-section in a direction transverse to the central axis of the tube.

9. A kit according to claim 8, wherein:
said seal has semi-elliptical ends.

10. A kit according to claim 1, wherein:
said seal has an ovoid cross-section in a direction transverse to the central axis of the tube.

11. A kit according to claim 1, wherein:
said seal has a blunt outer surface with only rounded features.

12. A kit according to claim 1, wherein:
said first maximal cross-sectional dimension is in the range between 0.4 mm and 0.7 mm, said second maximal cross-sectional dimension is no more than 0.4 mm, and said third maximal cross-sectional dimension is at least 0.9 mm.

13. A kit according to claim 1, wherein:
said tube is realized from a homogenous polymeric material, said polymeric material is selected from the group consisting of SIBS material, silicone rubber, a polyolefin polymer, a polyurethane polymer, an acrylic polymer, a fluoropolymer, a polyamide polymer, a hydrogel polymer, a biological based structure, a soft polymer foam material, a porous polymer material, and combinations thereof.

14. A kit according to claim 1, further comprising:
a device including a conduit sized to receive the tube of the aqueous humor drainage device, said conduit having a slot that allows passage of the tube of the aqueous humor drainage device therethrough.

15. A kit according to claim 1, further comprising:
a stylet sized for insertion into the tube of the aqueous humor drainage device in order to position the aqueous humor drainage device.

16. A method for surgical treatment of elevated ocular pressure of the eye, the method comprising:
providing the instrument having the needle body and the aqueous humor drainage device of the kit of claim 1;
inserting the needle body through tissue to define a tissue passage connected to the anterior chamber of the eye, wherein said needle body has a first maximal cross-sectional dimension along its length; and
inserting the aqueous humor drainage device into the tissue passage such that the distal end of the tube lies in the anterior chamber of the eye and the seal is disposed in the tissue passage and forms a seal between the tissue passage and the device and aqueous humor drains from the anterior chamber through the drainage device.

17. A method according to claim 16, wherein:
the tissue passage extends through scleral tissue, and the seal is disposed entirely within the scleral tissue.

18. A method according to claim 16, further comprising:
inserting a device into the tissue passage defined by the needle body, the device including a conduit sized to receive the tube of the aqueous humor drainage device, said conduit having a slot that allows for passage of the tube of the aqueous humor drainage device therethrough;
inserting the aqueous humor drainage device into the conduit; and
removing the conduit from the passage defined by the needle body while leaving behind the aqueous humor drainage device, whereby the slot of the conduit allows for passage of the tube of the aqueous humor drainage device therethrough during the removing.

19. A method according to claim 18, wherein:
the conduit is placed around a proximal part of the needle body and inserted into the tissue passage defined by the needle body as the tissue passage in formed by a distal part of the needle body.

* * * * *